United States Patent
Marchione et al.

(10) Patent No.: US 6,309,065 B1
(45) Date of Patent: Oct. 30, 2001

(54) DUAL LENS X-RAY PROTECTIVE EYEWEAR

(75) Inventors: Robert L. Marchione, P.O. Box 410, Randolph, VT (US) 05060; Anthony Skidmore, Randolph, VT (US)

(73) Assignee: Robert L. Marchione, Randolph, VT (US)

( * ) Notice: Subject to any disclaimer, the term of this patent is extended or adjusted under 35 U.S.C. 154(b) by 0 days.

(21) Appl. No.: 09/670,883

(22) Filed: Sep. 27, 2000

(51) Int. Cl.[7] ....................................... G02B 7/10
(52) U.S. Cl. ........................... 351/44; 351/41; 2/432
(58) Field of Search .................. 351/41, 158, 49, 351/44, 47, 57, 45, 46; 2/432, 426, 431

(56) References Cited

U.S. PATENT DOCUMENTS

| | | | |
|---|---|---|---|
| 5,016,292 | * | 5/1991 | Rademacher ..................... 2/432 |
| 5,140,710 | * | 8/1992 | Rademacher ..................... 2/432 |

* cited by examiner

Primary Examiner—Hung Xuan Dang
(74) Attorney, Agent, or Firm—William Nitkin

(57) ABSTRACT

X-ray protective eyewear is disclosed having dual lenses disposed within channels in each lens receipt area of the eyewear, the foremost lenses being transparent radiation-blocking lenses and the rearmost lenses being made of a plastic corrective or non-corrective lenses, as desired.

5 Claims, 1 Drawing Sheet

DUAL LENS X-RAY PROTECTIVE EYEWEAR

BACKGROUND OF THE INVENTION

1. Field of the Invention

The device of this invention resides in the field of radiation protective eyeglasses used during medical x-ray fluoroscopic procedures and more particularly relates to radiation protective eyewear having dual lenses placed in both the left and right side apertures of a pair of eyeglasses.

History of the Prior Art

During the past thirty years, while many new medical imaging technologies have been introduced and accepted, an older modality being x-ray fluoroscopy, which is almost as old as the x-ray itself, has quietly proliferated. X-ray fluoroscopy has become the imaging tool in many cases not only of choice, but also of necessity. It has become a tool not only of diagnosis, but also of treatment. Fluoroscopy which provides the ability to see within the body in real time has moved from simple x-ray diagnosis to use as a tool in a vast array of medical treatments.

With the evolution and proliferation of fluoroscopy, a large number of medical professionals have become engaged in its daily use as well as subject to its inherent problem which is exposure to radiation. Increasingly, nurses, surgeons, physicians and technologists, in addition to radiologists or radiologic technologists, are either working with fluoroscopy or present during it use.

While improving technology has decreased the radiation dose rates from what they were in the past, the use of fluoroscopy as a tool for treatment has expanded, requiring increased exposure times which often offset the radiation dose rate reductions realized by improved technology.

Thus, radiation safety is perhaps more of an issue today than twenty-five years ago. Increasingly, personnel who are involved in the performance of medical fluoroscopy procedures are wearing radiation protection eyewear.

Radiation protection eyewear lenses are generally made from a glass material that has been chemically combined with lead or other attenuating elements, and is commonly referred to as "lead glass." Unlike today's lightweight plastic material which is commonly used for lenses, this material is comparatively very heavy. Lead glass is also brittle and inclined to break easily when compared to either crown glass, that is used in glass ophthalmic lenses, or ophthalmic plastic lenses.

Although the risk of injury from lead glass lenses breaking due to an impact is relatively low, injuries can still occur as the risk of eye damage to one using lead glass ophthalmic lenses is much higher than the risk of injury to one when using plastic ophthalmic lenses. Therefore, the use of a plastic lens that could attenuate x-rays would be desirable. However, no suitable ophthalmic lens material providing comparable x-ray protection when compared to lead glass has been developed.

Another problem arises as many of the professionals who wear x-ray protective eyewear require corrective lenses, and prescription/corrective lead glass lenses are heavy as the weight of the lenses is increased due to thickening of the lenses required by such corrective lenses. As prescription ophthalmic lead glass lenses are increased in optical correction, they become unsuitably heavy in weight, rendering them difficult to wear, especially for prolonged periods of time.

SUMMARY OF THE INVENTION

It is a goal of this invention to provide an improved ergonomic and safe design for radiation protective eyewear. The design of this invention provides for a pair of eyeglasses into each single frame of which may be placed two lenses in front of each eye with a sealed space provided between each of the two lenses. This new frame design allows a plano or non-corrective radiation-blocking lens, such as a lead glass lens, to be placed in front of a plastic lens, thereby placing the plastic lens between the lead glass lens and the eye. This placement of the plastic lens enhances safety by making it less likely that the lead glass, if broken as a result of impact, could reach the eye of the wearer of the radiation protective eyeglasses of this invention. The eyeglasses of this invention also provide a sealed space between each pair of lenses which sealed space prevents dirt, moisture or other contaminants from entering therein and interfering with visual clarity.

Additionally, when a corrective lens is needed, the plastic lens can now serve as the corrective lens, while the lead glass lens can remain non-corrective and relatively thin and lightweight. This feature causes the overall weight of x-ray protective eyewear of this invention having plastic corrective lenses to be lighter in weight than the prior art conventional design in which only corrective lead glass lenses are used.

DESCRIPTION OF THE PREFERRED EMBODIMENT(S)

Figure 1:
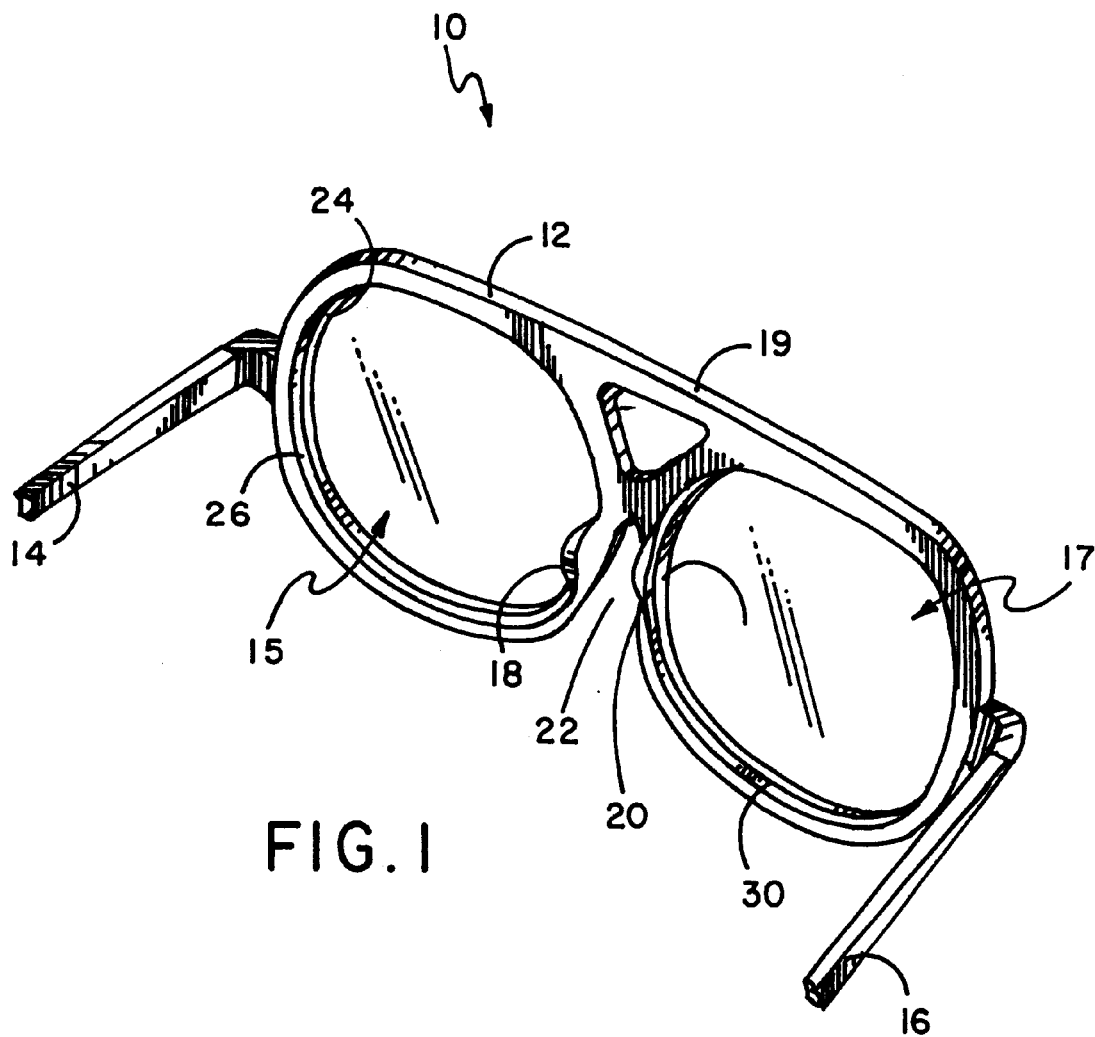
FIG. 1 illustrates a side perspective view of the x-ray protective eyewear of this invention having dual channels defined in each of the first and second eye portion frames for receipt of front lead glass lens and a rear plastic lens in each aperture thereof.

FIG. 1 illustrates a pair of typical safety glasses 10 having a frame 12 with first and second ear pieces 14 and 16 extending rearwardly therefrom to retain the glasses to the wearer's head. Other means of retaining the glasses to the wearer's head can also be utilized. Frame 12 can be of a conventional shape with two eye portion frames being first eye portion fame 15 and second eye portion frame 17, each having an aperture defined therein, and which are connected by bridge 19 having a nose receipt channel 22 formed thereunder. Disposed around nose receipt channel 22 are first nose rest 18 and second nose rest 20 which rest upon the nose of the wearer. Distinguishing the frame of this invention from those of the prior art is that it has a first pair of first front lens receipt channel 24 and first rear lens receipt channel 26 disposed around the inside of first eye portion frame 15 and a second pair of second front lens receipt channel 28 and second rear lens receipt channel 30 defined around the inside of second eye portion frame 17. Said first and second pairs of lenses are positioned, respectively, within the aperture of first eye portion frame 15 and the aperture of second eye portion frame 17 of the frame, in front of left and right eyes, respectively, of the wearer in the conventional manner.

Figure 2:
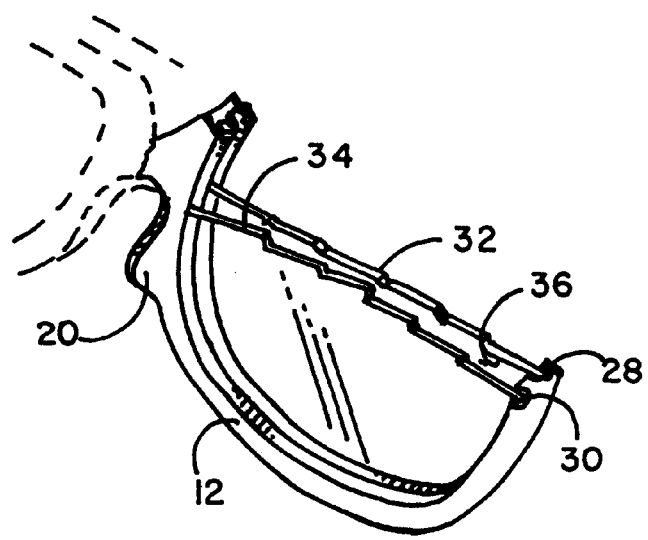
FIG. 2 illustrates a perspective view of the second eye portion frame of the eyewear of FIG. 1 with the upper portion thereof cut away to show the positioning of the dual lenses within the second front lens receipt channel and second rear lens receipt channel of the second eye portion frame.

FIG. 2 illustrates a perspective view of the second eye portion frame of the eyewear of FIG. 1 with the upper portion thereof cut away to show the positioning of the dual lenses within the second front lens receipt channel 28 and second rear lens receipt channel 30 of the second eye portion frame 17. Between the radiation-blocking lens 32 such as a lead glass lens and plastic lens 34 is defined a sealed space 36 which is sealed therearound by the body of second eye portion frame 17, not illustrated in this cutaway view of FIG. 2, such that dirt and other contaminants cannot make their way therein. In the same manner similar lenses can be placed within first front lens receipt channel 24 and first rear lens receipt channel 26 in front of the left eye of the wearer. Lightweight plastic lens 34 can be a non-corrective lens or a corrective lens while radiation-blocking lens 32 can be made of lead glass or an equivalent transparent radiation-blocking lens in a substantially flat, non-corrective lens which is much thinner and lighter in weight than corrective lead glasses, as previously discussed. Some radiation-blocking lenses can be curved to some extent. By the use of the dual channel frame and the introduction therein of a thin, non-corrected radiation-blocking lens and spaced to the rear thereof a lightweight plastic lens which can also be of a corrective type if needed by the wearer, the frame of this invention provides a lightweight pair of radiation protective eyewear which can be worn comfortably over prolonged periods of time.

Although the present invention has been described with reference to particular embodiments, it will be apparent to those skilled in the art that variations and modifications can be substituted therefor without departing from the principles and spirit of the invention.

What is claimed is:

1. An improved x-ray protective eyewear for use by a wearer, comprising:

an eyeglass frame having a first eye portion frame and a second eye portion frame, said first eye portion frame and said second eye portion frame each having an aperture defined therein, said first eye portion frame having a first front lens receipt area and first rear lens receipt area therein, said second eye portion frame having a second front lens receipt area and second rear lens receipt area therein, said front lens receipt area and said rear lens receipt area of each eye portion frame spaced apart a distance from one another;

a pair of first lenses, each being made of a transparent radiation-blocking material, each disposed within one of said front lens receipt areas in said eye portion frames;

a pair of second lenses, each being made of plastic, each disposed within one of said rear lens receipt areas, said pairs of first and second lenses disposed in said apertures of each of said first and second eye portion frames and forming, respectively, first and second spaces therebetween; and means to retain said eyewear on a wearer's head.

2. An improved x-ray protective eyewear for use by a wearer, comprising:

an eyeglass frame having a first eye portion frame and a second eye portion frame, said first eye portion frame and a second eye portion frame joined by a bridge member, said first eye portion frame and said second eye portion frame each having an aperture defined therein, said first eye portion frame having a first front lens receipt channel and first rear lens receipt channel defined therein, said second eye portion frame having a second front lens receipt channel and second rear lens receipt channel defined therein, said front lens receipt channel and said rear lens receipt channel of each eye portion frame spaced apart a distance from one another;

a pair of first lenses, each being made of a transparent radiation-blocking material, each disposed within one of said front lens receipt channels defined in said eye portion frames;

a pair of second lenses, each being made of plastic, each disposed within one of said rear lens receipt channels defined in said eye portion frames, said pairs of first and second lenses disposed in said apertures of each of said first and second eye portion frames and being surrounded by said first and second eye portion frames and forming, respectively, first and second sealed spaces therebetween; and means to retain said eyewear on a wearer's head.

3. The x-ray protective eyewear of claim 2 wherein each of said first lenses can be made of non-corrective lead glass.

4. The x-ray protective eyewear of claim 2 wherein each of said second lenses can be made of a corrective plastic lens.

5. The x-ray protective eyewear of claim 2 wherein each of said second lenses can be made of a non-corrective plastic lens.

* * * * *